United States Patent [19]

Lee et al.

[11] Patent Number: 4,925,984
[45] Date of Patent: May 15, 1990

[54] PARA-BROMINATION OF ORTHO-ALKYL ANILINES

[75] Inventors: John Y. Lee; Lawrence H. Shepherd, Jr., both of Baton Rouge, La.

[73] Assignee: Ethyl Corporation, Richmond, Va.

[21] Appl. No.: 191,349

[22] Filed: May 9, 1988

Related U.S. Application Data

[63] Continuation-in-part of Ser. No. 925,974, Nov. 3, 1986, abandoned.

[51] Int. Cl.$^5$ ............................................. C07C 85/24
[52] U.S. Cl. ..................................................... 564/412
[58] Field of Search ......................................... 564/412

[56] References Cited

PUBLICATIONS

Onaka et al "Selective Monobromination of Aniline Derivatives by use of Bromine Absorbed on Zeolite 5A", Chem. Lett., No. 11, p. 2007.

*Primary Examiner*—Dale R. Ore
*Attorney, Agent, or Firm*—Edgar E. Spielman, Jr.

[57] ABSTRACT

A process of selectively preparing p-bromo-o-alkylanilines (e.g. 4-bromo-2-methylaniline) by reacting o-alkylanilines (e.g., 2-methylaniline) with unadsorbed bromine in a solvent selected from the group consisting of an inert di- tri- or tetrahaloaliphatic hydrocarbon (e.g., dichloromethane and dibromomethane), an alkyl nitrile (e.g., acetonitrile) and mixtures thereof.

21 Claims, No Drawings

PARA-BROMINATION OF ORTHO-ALKYL ANILINES

REFERENCE TO RELATED APPLICATIONS

This is a continuation-in-part of prior copending application Ser. No. 925,974, filed Nov. 3, 1986, now abandoned.

BACKGROUND OF THE INVENTION

This invention relates to the preparation of p-bromo-o-alkylanilines by brominating o-alkylanilines.

Para-brominated o-alkylanilines, such as 4-bromo-2-methylaniline, have utility as intermediates in the preparation of herbicides, insecticides, fungicides, and plant growth regulators. A difficulty in brominating o-alkylanilines is that the aromatic ring of the anilines is usually polybrominated when reacted with bromine because the amino group of the aniline is highly activating. In addition, brominating o-alkylanilines with bromine can sometimes result in the bromination of the side chain substituents or the production of undesirable amounts of o-brominated o-alkylanilines, which are unacceptable as intermediates in certain applications.

Onaka, et al. describe in *Selective Monobromination of Aniline Derivatives by Use of Bromine Adsorbed on Zeolite 5A*, Chemistry Letters, No. 11, pages 2007–2008 (1984), The Chemical Society of Japan, a process which is said to obtain good selectivity in producing p-brominated-o-aniline. The process includes brominating aniline by use of molecular bromine adsorbed on Zeolite 5A.

The present invention resides in a method of selectively preparing high yields of p-brominated-o-alkylanilines.

SUMMARY OF THE INVENTION

The present invention provides a process for the production of p-bromo-o-alkylaniline by adding unadsorbed bromine to an o-alkylaniline-solvent solution, the solvent comprising an inert di-, tri- or tetra-halogenated aliphatic hydrocarbon, an alkyl nitrile or mixtures thereof. The unadsorbed bromine is generally added as a solute in any of the foregoing solvents. The use of the method of the invention results in the production of o-alkylanilines predominating in p-brominated isomers and only minor amounts of o-brominated isomers.

DETAILED DESCRIPTION OF THE INVENTION

The p-bromo-o-alkylanilines to which this invention pertains preferably are compounds having the formula:

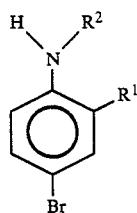

I wherein $R^1$ is an alkyl group having 1 to about 6 carbon atoms; and $R^2$ is selected from the group consisting of hydrogen, alkyl groups having 1 to about 18 carbon atoms, and alkoxyalkyl groups having from 1 to about 18 carbon atoms.

Preferably $R^1$ is an alkyl group having 1 to about 3 carbon atoms and $R^2$ is hydrogen or an alkyl group having 1 to about 3 carbon atoms. Exemplary $R^1$ and $R^2$ groups having 1 to about 3 carbon atoms include methyl, ethyl, propyl and isopropyl.

Examples of p-brominated o-alkylanilines corresponding to this formula include:

4-bromo-2-methylaniline
4-bromo-2-ethylaniline
4-bromo-2-propylaniline
4-bromo-2-isopropylaniline
4-bromo-2-n-butylaniline
4-bromo-2-t-butylaniline
4-bromo-2-sec-butylaniline
4-bromo-2-isobutylaniline
4-bromo-2-n-pentylaniline
4-bromo-2-t-pentylaniline
4-bromo-2-sec-pentylaniline
4-bromo-2-n-hexylaniline
4-bromo-2-isohexylaniline
N-methyl-4-bromo-2-methylaniline
N-ethyl-4-bromo-2-methylaniline
N-ethyl-4-bromo-2-ethylaniline
N-propyl-4-bromo-2-propylaniline
N-isopropyl-4-bromo-2-isopropylaniline
N-n-butyl-4-bromo-2-n-butylaniline
N-t-butyl-4-bromo-2-t-butylaniline
N-n-pentyl-4-bromo-2-n-pentylaniline
N-isopentyl-4-bromo-2-isopentylaniline
N-hexyl-4-bromo-2-hexylaniline
N-isohexyl-4-bromo-2-isohexylaniline
N-isohexyl-4-bromo-2-methylaniline
N-n-octyl-4-bromo-2-ethylaniline
N-isononyl-4-bromo-2-methylaniline
N-n-decyl-4-bromo-2-isopropylaniline
N-n-undecyl-4-bromo-2-methylaniline
N-n-dodecyl-4-bromo-2-t-butylaniline
N-n-tetradecyl-4-bromo-2-t-pentylaniline
N-n-pentadecyl-4-bromo-2-methylaniline
N-n-hexadecyl-4-bromo-2-ethylaniline
N-n-heptadecyl-4-bromo-2-isopropylaniline
N-n-octadecyl-4-bromo-2-n-butylaniline
N-pentyl-4-bromo-2-ethylaniline
N-isopropyl-4-bromo-2-methylaniline
N-methyl-4-bromo-2-pentylaniline
N-methoxyethyl-4-bromo-2-ethylaniline
N-propoxypropyl-4-bromo-2-hexylaniline
N-propoxyethyl-4-bromo-2-pentylaniline
N-isopropoxyethyl-4-bromo-2-methylaniline
N-n-butoxyethyl-4-bromo-2-ethylaniline
N-t-butoxyethyl-4-bromo-2-propylaniline
N-(2-ethoxy-1-methylethyl)-4-bromo-2-butylaniline
N-(2-ethoxy-2-methylethyl)-4-bromo-2-isohexylaniline
N-(3-methoxypropyl)-4-bromo-2-ethylaniline
N-(4-methoxybutyl)-4-bromo-2-n-propylaniline
N-propoxybutyl-4-bromo-2-methylaniline
N-ethoxyhexyl-4-bromo-2-methylaniline
N-ethoxyheptyl-4-bromo-2-ethylaniline
N-propoxyheptyl-4-bromo-2-pentylaniline
N-propoxyoctyl-4-bromo-2-pentylaniline
N-t-butoxyoctyl-4-bromo-2-methylaniline
N-n-pentoxyoctyl-4-bromo-2-propylaniline
N-n-hexoxyoctyl-4-bromo-2-methylaniline
N-n-hexoxynonyl-4-bromo-2-methylaniline
N-n-hexoxydecyl-4-bromo-2-methylaniline
N-n-heptoxydecyl-4-bromo-2-methylaniline N-n-octoxydecyl-4-bromo-2-propylaniline The process is carried out by reacting the o-alkylaniline with the unadsorbed bromine which is added to the o-alkylaniline-solvent solution. The o-alkylaniline preferably has the formula:

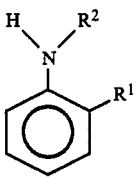

wherein $R^1$ and $R^2$ have the same meaning as they hold in Formula I. Examples of o-alkylanilines corresponding to Formula II include:
2-methylaniline
2-ethylaniline
2-propylaniline
2-isopropylaniline
2-n-butylaniline
2-t-butylaniline
2-sec-butylaniline
2-isobutylaniline
2-n-pentylaniline
2-t-pentylaniline
2-sec-pentylaniline
2-n-hexylaniline
2-t-hexylaniline
N-methyl-2-methylaniline
N-ethyl-2-methylaniline
N-ethyl-2-ethylaniline
N-propyl-2-propylaniline
N-isopropyl-2-isopropylaniline
N-n-butyl-2-n-butylaniline
N-t-butyl-2-t-butylaniline
N-n-pentyl-2-n-pentylaniline
N-isopentyl-2-isopentylaniline
N-hexyl-2-hexylaniline
N-isohexyl-2-isohexylaniline
N-isohexyl-2-methylaniline
N-n-octyl-2-ethylaniline
N-isononyl-2-methylaniline
N-n-decyl-2-isopropylaniline
N-n-undecyl-2-methylaniline
N-n-dodecyl-2-t-butylaniline
N-n-tetradecyl-2-t-n-pentylaniline
N-n-pentadecyl-2-methylaniline
N-n-hexadecyl-2-ethylaniline
N-n-heptadecyl-2-isopropylaniline
N-n-octadecyl-2-n-butylaniline
N-pentyl-2-ethylaniline
N-t-butyl-2-methylaniline
N-pentyl-2-methylaniline
N-t-butyl-2-methylaniline
N-isopropyl-2-methylaniline
N-methyl-2-pentylaniline
N-methoxyethyl-2-ethylaniline
N-ethoxyethyl-2-methylaniline
N-propoxypropyl-2-hexylaniline
N-isopropoxyethyl-2-pentylaniline
N-(n-butoxyethyl)-2-ethylaniline
N-(t-butoxyethyl)-2-propylaniline
N-(2-ethoxy-1-methylethyl)-2-butylaniline
N-(2-ethoxy-2-methylethyl)-2-methylaniline
N-(2-ethoxy-1-ethylethyl)-2-isohexylaniline
N-(3-methoxypropyl)-2-methylaniline
N-(4-methoxybutyl)-2-methylaniline
N-propoxybutyl-2-methylaniline
N-ethoxyhexyl-2-methylaniline
N-ethoxyheptyl-2-ethylaniline
N-propoxyheptyl-2-pentylaniline
N-propoxyoctyl-2-pentylaniline
N-t-butoxyoctyl-2-methylaniline
N-n-pentoxyoctyl-2-propylaniline
N-n-hexoxyoctyl-2-methylaniline
N-n-hexoxynonyl-2-methylaniline
N-n-hexoxydecyl-2-methylaniline
N-n-heptoxydecyl-2-methylaniline
N-n-octoxydecyl-2-propylaniline The solvent is preferably selected from the group consisting of an inert di-, tri-or tetra-halogenated aliphatic hydrocarbon having from 1 to about 4 carbon atoms, an alkyl nitrile having 2 to about 4 carbon atoms, and mixtures thereof. The reaction occurs at a temperature sufficient to cause bromination to proceed, but not so high as to cause decomposition of the reactants or products of the bromination. Examples of inert di- and tri-and tetra-halogenated aliphatic hydrocarbons having from 1 to about 4 carbon atoms which are suitable for use in the method of the invention include dihalomethanes such as dibromomethane, dichloromethane, diiodomethane and bromochloromethane, di- and trihaloethanes such as 1,1-dichloroethane, 1,2-dichloroethane, 1,1-dibromoethane, 1,2-dibromoethane, 1,1,1-trichloroethane, dihalopropanes such as 1,1- dichloropropane, 1,2-bromochloropropane, 1,2-diiodopropane, dihalobutanes such as 1,1-dichlorobutane, 1,2-dibromobutane and mixtures thereof. Other useful solvents include chloroform, bromoform, carbon tetrachloride, carbon tetrabromide, sym-tetrachloroethane, 1,1,1,2-tetrachloroethane and the like.

Examples of alkyl nitriles having 2 to about 4 carbon atoms which are suitable for use in the method of the invention include acetonitrile, propionitrile, butyronitrile, and mixtures thereof.

The preferred solvents for use in the method of the invention are dichloromethane, dibromomethane, acetonitrile and mixtures thereof.

As before noted, the bromine used in the process of this invention is unadsorbed bromine, i.e. the bromine is not adsorbed on a zeolite. The amount of unadsorbed bromine utilized in the method of the invention is an amount sufficient to brominate a portion of the o-alkylaniline in the para position. Preferably, the amount of unadsorbed bromine utilized is an amount in the range of from 0.5 to about 3.0 moles of unadsorbed bromine for each mole of o-alkylaniline. More preferably, the amount of unadsorbed bromine utilized is from about 0.75 to about 1.25 moles of unadsorbed bromine for each mole of o-alkylaniline. Most preferably, the amount is about 0.9 to about 1.1 moles of unadsorbed bromine for each mole of o-alkylaniline.

Preferably, the temperature used in the method of the invention is such that at least a portion of the o-alkylaniline is converted to p-bromo-o-alkylaniline. Preferably, the temperature range is from about −10° C. to about reflux and more preferably is from about 0° to about 50° C. and most preferably 0°-20° C.

The amount of solvent used in the method of the present invention is a solvent amount, preferably an amount of from about 100% to about 5000% by weight of the o-alkylanilines used in the method of the invention. More preferably, when a halogenated aliphatic hydrocarbon is utilized, an amount of from about 300% to about 5000% by weight of the o-alkylaniline is utilized and, most preferably, about 2000% by weight of the o-alkylaniline is utilized. More preferably, when an alkyl nitrile is utilized, an amount of from about 100% to about 2000% by weight of the o-alkylaniline is utilized, and, most preferably, about 1000% by weight of the o-alkylaniline is utilized.

The preferred compound prepared in the method of the invention is 4-bromo-2-methylaniline. Preferably, the method is carried out by reacting about 1 mole of 2-methylaniline in about 1 to about 2 liters of a solvent comprising either dichloromethane, dibromomethane, or acetonitrile with about 1.0 mole of unadsorbed bromine at a temperature in the range of from about 5° to 15° C. for a period of from about 10 to 40 minutes. Preferably, a basic material such as an alkali metal hydroxide, a mono-, di- or tri-alkyl amine, or anhydrous ammonia is added to the resulting solution in an amount sufficient to neutralize the HBr formed during the reaction.

When a halogenated aliphatic hydrocarbon solvent is utilized, preferably, the organic layer of the mixture is separated either from the aqueous layer or solid ammonium bromide. If present, the aqueous layer is, preferably, then washed with the solvent to remove any 4-bromo-2-methylaniline remaining in the water layer. Next, the combined organic layers are preferably washed with water and the organic layer is evaporated, preferably under reduced pressure to yield the solid 4-bromo-2-methylaniline.

When an alkyl nitrile such as acetonitrile is utilized as the solvent, anhydrous ammonia is preferably used to neutralize the HBr formed during the reaction. Next, ammonium bromide is removed from the mixture by filtration. After the removal of ammonium bromide, the alkylnitrile is stripped from the mixture and can be recycled. Next, the p-bromo-o-alkylaniline is recovered from the mixture by distillation.

It is a feature of the process of this invention that the unadsorbed bromine is added to the o-alkylaniline-solvent solution. The addition of the unadsorbed bromine is most effectively accomplished by first dissolving the unadsorbed bromine in a solvent of this invention prior to effecting the addition.

The present invention is further exemplified by the examples below which are presented to illustrate certain specific embodiments of the invention but are not intended to be construed so as to be restrictive of the spirit and scope thereof.

EXAMPLE 1

To several mixtures containing 1.07 grams (0.01 moles) of 2-methylaniline (2-MA) and varying amounts of dichloromethane, varying amounts of bromine were added with stirring over a period of about 20 minutes at a temperature from 5° to 10° C. The reaction mixtures were stirred an additional 30 minutes and a 10 gram aqueous solution containing 1.0 gram of sodium hydroxide was added to each mixture. The dichloromethane layer was separated from the aqueous layer of the mixtures. The aqueous layer was washed with dichloromethane and this dichloromethane layer was combined with the first dichloromethane layer. The combined dichloromethane layers were washed with 10 mL of water and evaporated at reduced pressure. The final product was analyzed using gas chromatography to determine the amount of 4-bromo-2-methylaniline (4-BMA), 2-bromo-6-methylaniline (2-BMA), and 2,4-dibromo-6-methylaniline (2,4-DBMA) present in the final product. The percent of 2-methylaniline converted to the final product is based on the amount of bromine utilized in the experiment and the results of these tests are set forth in Table 1.

TABLE I

| Test No. | $Br_2$ (moles) | $CH_2Cl_2$ (g) | Conversion[1] of 2-MA | Product Distribution (% by weight) | | |
|---|---|---|---|---|---|---|
| | | | | 4-BMA | 2-BMA | 2,4-DBMA |
| 1 | 0.01 | — | 68 | 71.8 | 8.5 | 19.7 |
| 2 | 0.03 | — | 81 | 67.0 | 5.5 | 27.5 |
| 3 | 0.01 | 10 | 87 | 85.2 | 2.8 | 12.0 |
| 4 | 0.03 | 10 | 87 | 78.4 | 1.9 | 19.7 |
| 5 | 0.01 | 20 | 87 | 86.8 | 1.8 | 11.4 |
| 6 | 0.03 | 20 | 78 | 82.6 | 1.3 | 16.1 |

[1]Mole % of 2-MA reacted to form a different product.

The results of these tests show that greater product selectivity to 4-BMA and reduced amounts of 2-BMA were obtained when dichloromethane was utilized as a solvent during the bromination of 2-MA.

EXAMPLE 2

To a mixture of 107 grams (1 mole) of 2-methylaniline (2-MA) and 2600 grams of dichloromethane was added 166 grams (1.04 mole) of bromine over a period of 30 minutes at a temperature in the range of from 5° to 10° C. The mixture was stirred during the addition and was stirred an additional 30 minutes after the addition of the bromine. Next, 650 grams of an aqueous solution containing 7% by weight sodium hydroxide was added to the mixture. Next, the dichloromethane layer of the mixture was separated from the aqueous layer. The aqueous layer was washed with 100 mL of dichloromethane. The two layers of dichloromethane were combined, washed with 100 mL of water, and vacuum distilled to recover 193 grams of product mixture. The product mixture was analyzed by proton NMR and vapor phase chromatography. The mixture contained 66.5 mole % of 4-bromo-2-methylaniline, 16.5 mole % of 2,4-dibromo-6-methylaniline, 17 mole % of 2-methylaniline and trace amounts of 2-bromo-6-methylaniline.

EXAMPLE 3

An amount of 53.5 grams (0.5 moles) of 2-methylaniline and 390 grams (500 mL) of acetonitrile were charged into a three-neck, 2 liter reactor. Next, 80 grams (0.5 moles) of bromine was fed into the reaction slurry under agitation at a temperature of 5° to 10° C. over a period of 30 minutes. Subsequently, excess ammonia gas was fed into the reaction slurry under agitation at a temperature of 10° to 12° C. in order to neutralize HBr from the aniline hydrobromide salts. A total of 48.2 grams of NH$_4$Br was then isolated by filtration. The filtrate was evaporated and yielded 89.4 grams of crude product. The crude product contained a mixture of 0.39 mole of 4-bromo-2-methylaniline, 0.055 mole of 2-methylaniline, 0.055 mole of 2,4-dibromo-6-methylaniline and trace amounts of 2-bromo-6-methylaniline.

The crude mixture was separated by fractional distillation through a column having ten theoretical plates to give 6.0 grams (0.056 mole) of 2-methylaniline at 43° C./1 mm torr, 69.2 grams (0.372 mole) of 4-bromo-2-methylaniline at 83° C./1 mm torr, and 14.3 grams (0.054 mole) of 2,4-dibromo-6-methylaniline as a pot residue.

Although certain preferred embodiments of the invention have been herein described for illustrative purposes, it will be appreciated that various modifications of the procedures of compositions recited may be effected without departure from the basic principles which underlie the invention.

What is claimed:

1. A method of preparing a product predominant in p-bromo-o-alkylaniline, which process comprises, reacting an o-alkylaniline with unadsorbed bromine in a solvent selected from the group consisting of an inert di-, tri- or tetra-halogenated aliphatic hydrocarbon having from 1 to about 4 carbon atoms, an alkyl nitrile having 2 to about 4 carbon atoms, and mixtures thereof at a temperature sufficient to convert at least a portion of said o-alkylaniline to said p-bromo-o-alkyl-aniline.

2. The method of claim 1 wherein the reaction of said o-alkylaniline and said unadsorbed bromine is effected by adding said unadsorbed bromine to a solution comprising said solvent and said o-alkylaniline.

3. The method of claim 2 wherein said solvent is selected from the group consisting of dibromomethane, dichloromethane, chloroform, bromoform, carbon tetrachloride, bromochloromethane, 1,1-dichloroethane, 1,2-dichloroethane, 1,1-dibromoethane, 1,2-dibromoethane, 1,1,1-trichloroethane, 1,1,2-trichloroethane, sym-tetrachloroethane 1,1-dichloropropane, 1,2-bromochloropropane, 1,1-dichlorobutane, 1,2-dibromobutane, acetonitrile, propionitrile, butyronitrile, and mixtures thereof.

4. The method of claim 2 wherein said o-alkylaniline has the formula:

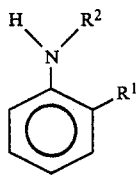

II wherein $R^1$ is an alkyl group having 1 to about 6 carbon atoms; and, $R^2$ is selected from the group consisting of hydrogen, an alkyl group having 1 to about 18 carbon atoms and an alkoxyalkyl group having 1 to about 18 carbon atoms.

5. The method of claim 4 wherein $R^1$ is an alkyl group having 1 to about 3 carbon atoms and $R^2$ is hydrogen.

6. The method of claim 4 wherein said temperature is in the range of from 0° to about 50° C.

7. The method of claim 4 wherein said unadsorbed bromine is present in an amount in the range of from about 0.75 to about 1.25 moles of said unadsorbed bromine per mole of said o-alkylaniline.

8. The method of claim 4 wherein said solvent is present in an amount in the range of from about 100 to about 5000% by weight of said o-alkylaniline.

9. The method of claim 4 wherein said o-alkylaniline is 2-methylaniline.

10. The method of claim 9 wherein said solvent is dichloromethane, acetonitrile or mixtures thereof.

11. The method of claim 10 wherein said temperature is in the range of from 0° to about 20° C.

12. The method of claim 11 wherein said solvent is acetonitrile.

13. The method of claim 11 wherein said solvent is dichloromethane.

14. The method of claim 12 wherein said unadsorbed bromine is present in an amount in the range of from about 0.75 to about 1.25 moles of said unadsorbed bromine per mole of said o-alkylaniline.

15. The method of claim 14 wherein said solvent is present in an amount in the range of from about 100 to about 5000% by weight of said o-alkylaniline.

16. The method of claim 13 wherein said unadsorbed bromine is present in an amount in the range of from about 0.75 to about 1.25 moles of said unadsorbed bromine per mole of said o-alkylaniline.

17. The method of claim 16 wherein said solvent is present in an amount in the range of from about 100 to about 5000% by weight of said o-alkylaniline.

18. The method of claim 2 further comprising adding anhydrous ammonia to said solution.

19. The method of claim 4 further comprising adding anhydrous ammonia to said solution.

20. The method of claim 15 further comprising adding anhydrous ammonia to said solution.

21. The method of claim 17 further comprising adding anhydrous ammonia to said solution.

* * * * *